United States Patent
Lehtonen et al.

(10) Patent No.: US 6,593,329 B1
(45) Date of Patent: Jul. 15, 2003

(54) METHOD FOR THE TREATMENT OR PREVENTION OF CORONARY GRAFT VASOSPASM

(75) Inventors: Lasse Lehtonen, Espoo (FI); Julius Papp, Szeged (HU); Janos Szecsi, Szeged (HU)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/019,392

(22) PCT Filed: Jun. 29, 2000

(86) PCT No.: PCT/FI00/00592

§ 371 (c)(1),
(2), (4) Date: May 30, 2002

(87) PCT Pub. No.: WO01/00211

PCT Pub. Date: Jan. 4, 2001

(30) Foreign Application Priority Data

Jun. 29, 1999 (GB) .............................................. 9915179

(51) Int. Cl.⁷ .............................................. A61K 31/50
(52) U.S. Cl. ...................................................... 514/247
(58) Field of Search ........................................ 514/247

(56) References Cited

FOREIGN PATENT DOCUMENTS

| EP | 0 565 546 | 10/1993 |
|----|-----------|---------|
| WO | 92/12135 | 7/1992 |
| WO | 93/21921 | 11/1993 |

OTHER PUBLICATIONS

DRUGU AN 2000–03016, Pataricza J et al, Fundam. Clin. Pharmacol., 13, Suppl. 1, 231s, 1999, abstract.*

Lilleberg et al., "Effects of a new calcium sensitizer, levosimendan, on haemodynamics, coronary blood flow and myocardial substrate utilization early after coronary artery bypass grafting." European Heart Journal, vol. 19, pp. 660–668 (1998).

Nijhawan et al., "Levosimendan Enhances Cardiac Performance After Cardiopulmonary Bypass: A Prospective, Randomized Placebo–Controlled Trial," Journal of Cardiovascular Pharmacology, vol. 34, pp. 219–228 (1999).

Lochner et al., "Effect of a Calcium–Sensitizing Agent, Levosimendan, on the Postcardioplegic Inotropic Response of the Myocardium," Cardiovascular Drugs and Therapy, vol. 14, pp. 271–281 (2000).

Sonntag et al., "Effects of the Calcium Sensitizer Levosimendan on Stunned Myocardium after Percutaneous Transluminal Coronary Angioplasty," Circulation, vol. 110, supp. 18, p. I–79 (Nov. 1999).

Database STN International, Nijhawan et al., "Levosimendan Enhances cardiac performance in patients undergoing cardiac surgery: a double–blind trial," from FILE Adisalerts, accession No. 1998) 1199; Doc 800671118, XP002901278 abstract & Anethesia and Analgesia, vol. 86, Apr. 1, 1998, p. 31.

* cited by examiner

*Primary Examiner*—Rebecca Cook
(74) *Attorney, Agent, or Firm*—Finnegan, Henderson, Farabow, Garrett & Dunner, LLP

(57) ABSTRACT

Levosimendan, or (−)-[[4-(1,4,5,6-tetrahydro-4-methyl-6-oxo-3-pyridazinyl)phenyl]hydrazono]-propanedinitrile, which has been previously suggested for the treatment of congestive heart failure is useful in the treatment or prevention of coronary graft vasospasm after coronary artery by-pass surgery.

9 Claims, No Drawings

METHOD FOR THE TREATMENT OR PREVENTION OF CORONARY GRAFT VASOSPASM

This application is a national stage filing of PCT International Application No. PCT/FI00/00592, filed on Jun. 29, 2000, which published in the English language. This application also claims the benefit of priority to patent application no. 9915179.1, filed in Great Britain on Jun. 29, 1999.

TECHNICAL FIELD

The present invention relates to a method for the treatment or prevention of coronary graft vasospasm after coronary artery by-pass surgery by administering levosimendan, or (−)-[[4-(1,4,5,6-tetrahydro-4-methyl-6-oxo-3-pyridazinyl)phenyl]-hydrazonopropanedinitrile (I), or pharmaceutically acceptable salts thereof, to a patient in need of such prevention or treatment.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B 1. Levosimendan is potent in the treatment of heart failure and has significant calcium dependent binding to troponin. Levosimendan is represented by the formula:

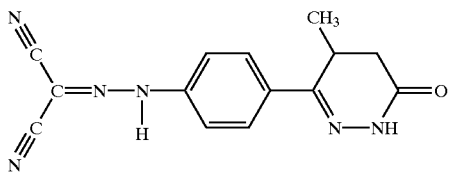

I

The hemodynamic effects of levosimendan in man are described in Sundberg, S. et al., Am. J. Cardiol., 1995; 75: 1061–1066 and in Lilleberg, J. et al., J. Cardiovasc. Pharmacol., 26(Suppl.1), S63–S69, 1995. Pharmacokinetics of levosimendan in man after i.v. and oral dosing is described in Sandell, E.-P. et al., J. Cardiovasc. Phannacol., 26(Suppl.1), S57–S62, 1995. The use of levosimendan in the treatment of myocardial ischemia is described in WO 93/21921. Clinical studies have confirmed the beneficial effects of levosimendan in heart failure patients.

Coronary artery disease (CAD) is very common, particularly in older age groups. One of the main therapies of symptomatic CAD is coronary surgery. This is relatively simple and cost-effective treatment of main artery occlusions. However, in many patients coronaries are affected by multiple occlusions. In these cases, the availability of intact vessel for grafts becomes an issue and quite often the grafts are stretched to make anastomoses over the whole affected area Surgical manipulation of the vascular graft or its stretching, however, may induce a vasospasm that may complicate the blood flow to the reperfused areas. Sometimes the occlusion caused by the spasm is so severe that emergency surgery has to be carried out to prevent myocardial infarction.

At the moment, there are no well established treatments of coronary graft vasospasms. In some centers, calcium antagonists are used. They, however, due to their negative inotropic properties, may reduce cardiac output and induce a postoperative heart failure. Drugs having ability to prevent graft vasospasms would be very useful in the postoperative management of patients who undergo coronary artery by-pass grafting.

SUMMARY OF THE INVENTION

It has now been found that levosimendan is able to prevent coronary graft vasospasm after coronary artery by-pass surgery.

Therefore, the present invention provides the use of (−)-[[4-(1,4,5,6-tetrahydro-4-methyl-6-oxo-3-pyridazinyl)phenyl]hydrazono]propanedinitrile or a pharmaceutically acceptable salt thereof in the manufacture of a medicament for the treatment or prevention of coronary graft vasospasm.

The present invention also provides a method for the treatment or prevention of coronary graft vasospasm in a patient, said method comprising administering to a patient in need thereof an effective amount of (−)-[[4-(1,4,5,6-tetrahydro-4-methyl-6-oxo-3-pyridazinyl)phenyl]hydrazono]propanedinitrile or a pharmaceutically acceptable salt thereof.

DETAILED DESCRIPTION

The method of the invention comprises a step of administering to a subject an amount of levosimendan effective to prevent coronary graft vasospasm. The administration can be effected enterally, e.g. orally or rectally, or parenterally, e.g. intravenously or transdermally. The effective amount of levosimendan to be administered to a subject depends upon the condition to be treated, the route of administration, age, weight and the condition of the patient. In general levosimendan is administered orally to man in daily dose from about 0.1 to 20 mg, preferably from 0.2 to 15 mg, more preferably from 0.5 to 10 mg, given once a day or divided into several doses a day, depending on the age, body weight and condition of the patient. Levosimendan can be administered by intravenous infusion using the infusion rate typically from about 0.01 to 10 $\mu$g/kg/min, more typically from about 0.02 to 5 $\mu$g/kg/min. For example, using an infusion of 24 hours a rate of 0.05–0.2 $\mu$g/kg/min is considered suitable.

Levosimendan can be administered to a patient before, during or after the bypass operation. Preferably the administration of levosimendan is started, e.g. intravenously with the infusion range as described above, after the coronary bypasses are completed and the patient is weaned from the heart-lung machine. Preferably, the infusion of levosimendan is continued throughout the early recovery period, i.e. till the patient is extubated to prevent coronary graft vasospasm.

Levosimendan is formulated into dosage forms suitable for the treatment or prevention of coronary graft vasospasm using the principles known in the art. It is given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.1 to 10 mg, more typically 0.2 to 5 mg, of levosimendan.

Formulations suitable for intravenous administration such as injection or infusion formulation, comprise sterile isotonic solutions of levosimendan and vehicle, preferably aqueous solutions. Typically an intravenous infusion solution comprises from about 0.01 to 0.1 mg/ml of levosimendan.

Salts of levosimendan may be prepared by known methods. Pharmaceutically acceptable salts are useful as active medicaments, however, preferred salts are the salts with alkali or alkaline earth metals.

EXAMPLES

Experiment 1

The effect of levosimendan to prevent vasospasm was investigated in human internal mammary artery (IMA) preparations from coronary by-pass surgery (8 patients) at three different levels of vascular tone using isolated ring technique. It is known that IMA may produce spasm during and after graft surgery especially at low perfusion pressure (at or lower than 50 mmHg).

Isometric stretch was applied perpendicular to the direction of blood flow for 45 min in organ bath containing oxygenated Krebs-Henseleit solution (37° C., pH 7.4). Magnitude of stretch (in mN) was converted into quasi-equivalent pressure values (23, 46 and 92 mmHg) according to the Laplace law. Isolated IMA rings were contracted with noradrenaline (1–10 $\mu$M), and at the steady state contraction, levosimendan (0.3 and 0.6 $\mu$M) was added cumulatively.

The results are shown in Table 1. The results show that levosimendan prevents graft vasospasm in clinically relevant submicromolar concentrations, and in particular at the clinically dangerous low perfusion pressure values.

TABLE 1

Effect of levosimendan on coronary graft vasospasm at different transmural pressures
(nd = not determined)

| | Prevention (%) of graft vasospasm (as % of maximal attainable spasm) at | | | | | |
|---|---|---|---|---|---|---|
| | 23 mmHg Levosimendan | | 46 mmHg Levosimendan | | 92 mmHg Levosimendan | |
| Patient | 0.3 $\mu$M | 0.6 $\mu$M | 0.3 $\mu$M | 0.6 $\mu$M | 0.3 $\mu$M | 0.6 $\mu$M |
| 1. | 46.1 | 76.9 | 28.6 | 85.7 | 16.6 | 61.6 |
| 2. | nd | 125.0 | 75.0 | 100.0 | 0 | 22.0 |
| 3. | 27.2 | 45.5 | 13.8 | 41.4 | 3.9 | 14.9 |
| 4. | 37.5 | 62.5 | 8.3 | 27.1 | 8.2 | 34.7 |
| 5. | nd | 0 | 57.1 | 114.3 | 9.6 | 26.7 |
| 6. | 60.0 | 110.0 | 16.2 | 21.6 | nd | nd |
| 7. | 46.7 | 113.3 | 37.8 | 78.4 | nd | nd |
| 8. | 40.0 | 113.0 | 17.3 | 57.7 | nd | nd |
| Mean | 42.9 ± 4.5 | 80.8 ± 15.3 | 31.8 ± 8.3 | 65.8 ± 12.1 | 7.7 ± 3.8 | 32.0 ± 8.1 |

Pharmaceutical example.

| Hard gelatin capsule size 3 | |
|---|---|
| Levosimendan | 2.0 mg |
| Lactose | 198 mg |

The pharmaceutical preparation in the form of a capsule was prepared by mixing levosimendan with lactose and placing the powdery mixture in hard gelatin capsule.

What is claimed is:

1. A method for the treatment or prevention of coronary graft vasospasm in association with coronary artery bypass surgery in a patient, said method comprising administering to a patient in need thereof an effective amount of (−)-[[4-(1,4,5,6-tetrahydro-4-methyl-6-oxo-3-pyridazinyl)phenyl]hydrazono]prpanedinitrile or a pharmaceutically acceptable salt thereof.

2. The method according to claim 1, wherein the administration is intravenous.

3. The method according to claims 1, wherein the administration is started after the coronary bypass surgery is completed.

4. The method according to claim 1, wherein the administration is continued throughout the patient's early recovery period following the surgery.-

5. The method according to claim 2, wherein the administration is started after the coronary bypass surgery is completed.

6. The method according to claim 2, wherein the administration is continued throughout the patient's early recovery period following the surgery.

7. The method according to claim 3, wherein the adrministration is continued throughout the patient's early recovey period following the surgery.

8. The method according to claim 1, which comprises the treatment of coronary graft vasospasm in association with coronary artery bypass surgery in the patient.

9. The method according to claim 1, which comprises the prevention of coronary graft vasospasm in association with coronary artery bypass surgery in the patient.

* * * * *

UNITED STATES PATENT AND TRADEMARK OFFICE
CERTIFICATE OF CORRECTION

PATENT NO. : 6,593,329 B1
DATED : July 15, 2003
INVENTOR(S) : Lasse Lehtonen et al.

It is certified that error appears in the above-identified patent and that said Letters Patent is hereby corrected as shown below:

<u>Column 4,</u>
Line 57, "hydrazono]prpanedinitrile" should read -- hydrazono]propanedinitrile --.
Line 62, "claims" should read -- claim --.
Line 67, "surgery.-" should read -- surgery. --.

<u>Column 5,</u>
Lines 7-8, "adrministration" should read -- administration --.

Signed and Sealed this

Second Day of September, 2003

JAMES E. ROGAN
*Director of the United States Patent and Trademark Office*